United States Patent [19]
Johnson et al.

[11] Patent Number: 4,860,744
[45] Date of Patent: Aug. 29, 1989

[54] THERMOELECTRICALLY CONTROLLED HEAT MEDICAL CATHETER

[75] Inventors: Norman J. Johnson, Lexington, Mass.; Raj K. Anand, 210 Lincoln St., Worcester, Mass. 01605

[73] Assignee: Raj K. Anand, Worcester, Mass.

[21] Appl. No.: 116,526

[22] Filed: Nov. 2, 1987

[51] Int. Cl.$^4$ .............................................. A61B 17/38
[52] U.S. Cl. ................. 128/303.1; 128/401; 62/3.2
[58] Field of Search .............. 128/303.1, 401; 62/3, 62/293

[56] References Cited

U.S. PATENT DOCUMENTS

| | | | |
|---|---|---|---|
| 3,207,159 | 9/1965 | Tateisi | 128/303.1 |
| 3,502,080 | 3/1970 | Hirschhorn | 128/303.1 |
| 4,032,363 | 6/1977 | Raag | 136/211 |
| 4,445,892 | 5/1984 | Hussein | 604/101 |
| 4,483,341 | 11/1984 | Witteles | 128/303.1 X |
| 4,512,762 | 4/1985 | Spears | 604/21 |
| 4,519,389 | 5/1985 | Gudkin et al. | 128/303.1 |
| 4,519,390 | 5/1985 | Horne | 128/303.1 |
| 4,528,979 | 7/1985 | Marchenko et al. | 128/303.1 X |
| 4,576,177 | 3/1986 | Webster | 128/660 |
| 4,580,557 | 4/1986 | Hertzmann | 128/303.1 |
| 4,587,972 | 5/1986 | Morantte | 128/660 |
| 4,627,436 | 12/1986 | Leckrone | 128/303.1 |
| 4,654,024 | 3/1987 | Crittenden et al. | 128/303.1 X |
| 4,672,962 | 6/1987 | Herschenson | 128/303.1 |

FOREIGN PATENT DOCUMENTS

3119322 1/1983 Fed. Rep. of Germany .
3502331 8/1985 Fed. Rep. of Germany .

OTHER PUBLICATIONS

PCT/US84/00902 Hussein 12/20/84.
PCT/US82/01669 Garrett 06/09/83.

*Primary Examiner*—Lee S. Cohen
*Attorney, Agent, or Firm*—Lorusso & Loud

[57] ABSTRACT

A system and method are disclosed for providing precisely controlled heating (and cooling in come case) of a small region of body tissue to effectuate the removal of tumors and deposits. Such as atheromatous plaque, without causing damage to healthy surrounding tissue, e.g. arterial walls. Such precisely controlled heating is produced through thermoelectric and resistive heating, and thermoelectric control of a heated probe tip. The system includes a probe tip with N-doped and P-doped legs of seminconductor material, a catheter to which the probe tip is attached for insertion into a patient's body, and a system control mechanism. The probe may be used for reduction and/or removal of atheromatous obstruction in arteries or veins. It may also be used for destruction of diseased tissue and/or tumors in various parts of the body, such as the brain or the bladder. The probe may be configured for either tip heating or for side heating.

32 Claims, 7 Drawing Sheets

FIG. 6

THERMOELECTRICALLY CONTROLLED HEAT MEDICAL CATHETER

BACKGROUND OF THE INVENTION

I. Field of the Invention

This invention relates to a system for the removal of undesirable deposits within a patient's body and, more particularly, to a system for the application of highly-controlled, localized heat to precise points within a patient's body for the removal of undesirable deposits such as atheromatous plaque or a blood clot within arteries and for the removal of tumors.

II. Description of the Prior Art

There are a number of techniques known for remedying the problems associated with undesirable deposits within a patient's body such as atheromatous plaque within arteries. One such technique is balloon angioplasty which results in recanalization of the artery. This method is not well understood but it is believed that the plaque splits and gets partially embedded into the media of the vessel walls. There are a number of problems with this procedure since the plaque is not actually removed. One such problem is that the remnant of the procedure is a nidus for restenosis.

The problems associated with balloon angioplasty have led to the development of procedures for physically removing the plaque. Removal of the plaque can be achieved either by atherectomy (cut and retrieve) using an atherectomy device or by atherolysis (vaporization of plaque). The latter procedure has been preferred since it causes less trauma to the arterial wall and leaves behind a relatively smoother surface which may significantly reduce the incidence of restenosis. Moreover, such a device can also be used to recanalize a completely obstructed artery.

A number of devices are used for atherolysis with varying degrees of success. Such devices are physically coupled to a laser source with the laser beam being used as a heat source. One problem associated with the use of direct laser energy for atherolysis is that arterial wall perforation can result.

A hot tip laser probe, where the metal tip of a metal tip catheter is internally heated by an argon laser, has been used for atherolysis. The laser device is coupled to the metal tip with a thin optical fiber making the system compatible with catheters. A number of problems have been associated with the use of the hot laser tip probe. One problem is that the exact tip contact temperature is difficult (if not impossible) to monitor adequately, thereby potentially causing damage to the arterial wall when the tip is heated to temperatures that are too extreme. Another problem is that temperatures at the tip fluctuate, making it difficult to control removal of the plaque, particularly if it is calcified. Finally, the system is very expensive.

Another method to destroy atheromatous plaque involves injecting a hematoporphyrin into a patient for selective uptake into the atheromatous plaque. Light is delivered to the diseased vessel so that the light activates the hematoporhyrin and lysis of the plaque results.

Tumors are treated in several ways. Surgical removal of internal tumors in humans is a long established medical technique for removing undesirable growths within a patient's body. This technique often involves deep penetration and prolonged open procedures that increase patient trauma and sepsis hazard. The wide variety of techniques which have been developed include cryogenic and heated probes.

Hyperthermia is one such heating process which heats the tumor to 40° C. and denatures the enzymes associated with the tumorous cell causing the tumor cells to lyse. Volume heating of a tumor is achieved with lasers. Nd-YAG lasers are preferred for their ability to deeply penetrate tissue because they are poorly absorbed by tissue and have a high level of scattering. Heating (or burning) is also employed for surgery and removing unwanted tissue such as warts.

A significant disadvantage of known heating techniques is that the heating device cools down slowly. The heating device must be cooled down before it is removed from a patient's body in order to prevent damage to adjacent tissue and to prevent damage to the catheter itself. Consequently, an extensive cooldown period before the device can be removed may result in excessive heating of tissue and lengthy treatment time.

New techniques and materials which obviate the problems of the known methods and devices are desired.

SUMMARY OF THE INVENTION

The present invention is a method and apparatus for providing precisely controlled heating (and cooling in some cases) of a small region of body tissue to effectuate the removal of deposits, such as atheromatous plaque, clots, and tumors without causing significant damage to healthy surrounding tissue, e.g. arterial walls. Such precisely controlled heating is produced through thermoelectric and resistive heating, and thermoelectric measurement of a heated probe tip. After the treatment is completed, the probe tip can be rapidly cooled to avoid further heating of tissue and to facilitate removal of the device. The apparatus comprises a heated probe tip, a catheter or other means for accommodating the probe tip, and a control mechanism. This system may be used for reduction and/or removal of atheromatous obstructions in arteries or veins. It may also be used for destruction of diseased tissue and/or tumors in various parts of the body, such as the brain or the bladder.

The probe tip utilizes a thermoelectric element which includes positive (P) and negative (N) doped elements formed of semiconductor materials such as an alloy of silicon-germanium which is stable at temperatures up to about 1,000° C. The thermoelectric element may be configured for either tip heating or for side heating. The side heating embodiment can include an inflatable balloon(s) for pressing the side heated probe against the undesirable deposit.

Accordingly, it is an object of the present invention to provide a method and apparatus for eliminating harmful organic material from a patient's body without damaging the patient.

It is another object of the present invention to provide a method and apparatus for the application of highly controlled reversible localized heating or cooling to precise points within a patient's body to eliminate harmful organic material such as atheromatous plaque and tumors.

Another object of the present invention is to provide a catheter which produces a highly controlled, localized heat where a semiconductor material is used to produce the heat.

Another object of the present invention is to provide a heated catheter which is capable of rapid cooling.

Yet another object of the present invention is to provide a method and apparatus for the application of highly controlled, localized heat which feeds the temperature of the localized heat back to a temperature comparator as a means to regulate the operating temperature.

These and other objects and features of the present invention will be more fully understood from the following detailed description which should be read in light of the accompanying drawing in which corresponding reference numerals refer to corresponding parts throughout the several views.

DESCRIPTION OF THE PREFERRED EMBODIMENTS

At the outset, the invention is described in its broadest overall aspects with a more detailed description following. The broadest aspects of the invention involve applying highly controlled localized heat (or cooling) to precise points within a patient's body in order to eliminate harmful organic material in a patient's body without damaging other tissues. The device permits rapid and reversible heating and cooling of a probe tip to destroy selected tissue or to melt or vaporize deposits in a patient's artery such as atheromatous plaque. The device may be inserted within a catheter sheath or a hypodermic needle and may be combined with a balloon. The purpose of the balloon is to press the device against the side of the patient's artery.

As used throughout the specification and claims, the term "catheter" is intended to define a long tubular structure for housing a device for medical treatment which can be inserted into a patient's body. The particular device, in accordance with the present invention, incorporated in the catheter for the medical treatment of a patient is termed a "probe".

One important embodiment of the present invention builds on the prior discovery that atheromatous plaque can be physically removed from blood vessel walls by applying high heat to the plaque whereby the plaque melts or vaporizes. The device of the present invention utilizes a unique thermocouple to liquify or vaporize plaque.

Generally, thermocouples are temperature measuring devices consisting of two lengths or "legs" of differing materials. These materials are selected to have as large a difference in electromotive potential as possible for the operational temperature range. This can be achieved with semiconductors by doping the two parts (adding minute amounts of a donor or acceptor material) to produce positive (P) and negative (N) types. The two legs are joined at one end. This junction is placed where the temperature is to be measured. The other end of the legs is monitored by a measuring instrument and kept at a constant lower temperature. The temperature difference between the two ends causes the development of an electromotive force (known as the Seebeck effect) that is approximately proportional to the difference between the temperature at the two ends. A measuring instrument, which measures this electromotive force, can be calibrated to read the temperature output directly.

A thermocouple may also be used to produce heat. When current flows through the circuit containing the differing conductors, one junction between the materials is cooled while the other is heated. The direction of the current determines which junction is cooled and which is heated. This phenomenon is called the Peltier effect and is essentially the inverse of the Seebeck effect.

A problem with the use of thermocouples as practical heat sources has been that known materials could not produce sufficient heat or electricity when used in small configurations. However, developments in the area of thermocouple design have led to concepts for producing electrical power from heat by means of thermoelectricity. For example, U.S. Pat. No. 4,032,363 to Raag, the teachings of which are incorporated herein by reference, discloses a small-dimensioned electrical power generating array of a semiconductor thermopile for producing low values of electrical power at high values of direct output voltage.

The probe 1 of the present invention utilizes a thermoelectric element 7 to produce heat (or cooling if the current is reversed). The materials of the thermoelectric element 7 may be configured in a variety of different ways such as bar or wire forms or unicouple or multicouple designs. The thermoelectric element 7 can be constructed from metals or semiconductors with high thermoelectric potential differences as a function of temperature. A preferred embodiment utilizes thermocouples created from a silicon-germanium alloy doped with suitable doping materials, i.e. gallium phosphide, to produce positive (P-type) legs and negative (N-type) legs. In addition to any of various alloys of silicon and germanium, pure silicon may also be employed in forming the element 7. The P and N legs are distinguished by the extent to which the silicon-germanium alloy or other material is doped. The manner in which P and N legs are formed is known to those skilled in the art and forms no part of the present invention.

Figure 2A:
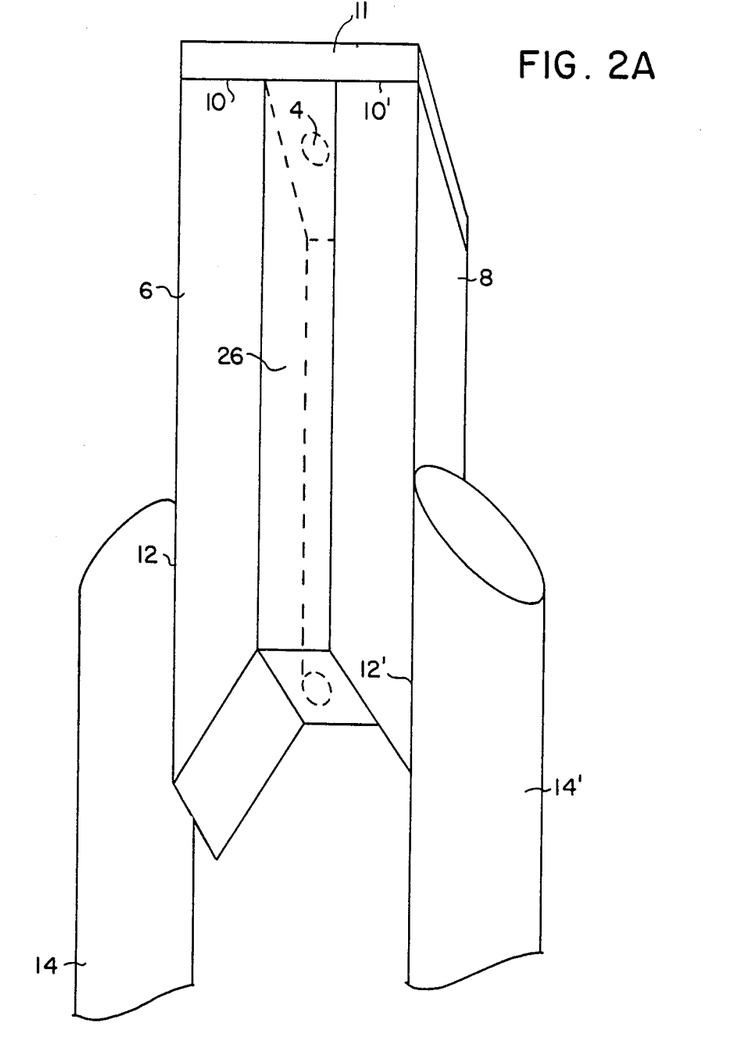
FIG. 2A is a partial view in perspective of a unicouple design for the thermoelectric element in FIG. 1 showing the spatial relationship between the electrodes, the connector wires, the probe tip junction, and the reference junctions.

A unicouple design, shown in FIG. 2A, utilizes one pair of P and N legs. The P leg 6 and N leg 8 are electrically separated along their lengths, but are joined at one end. The P and N legs 6, 8 are separately connected at a second end to connector wires 14, 14'. The ends of the thermocouple are referred to as junctions. The probe tip junctions 10, 10' represent one set of junctions. The other set of junctions are the reference junctions 12, 12'.

Figure 2B:
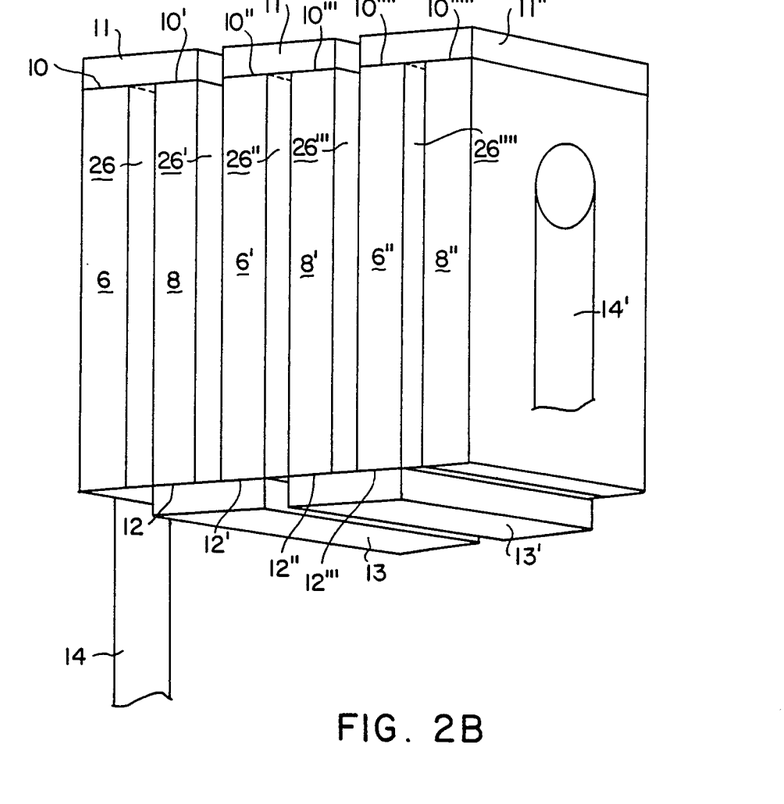
FIG. 2B is a partial view in perspective of a multicouple design for the thermoelectric element of a probe in accordance with the invention showing the spatial relationship between the electrodes, the connector wires, the probe tip junctions, and the reference junctions.

FIG. 2B illustrates a second embodiment for the thermoelectric element 7 which incorporates a multicouple design. The alternating P 6, 6', 6" and N 8, 8', 8" doped silicon-germanium alloy legs, are electrically separated along their lengths, but are joined at each end in pairs, referred to as couples, P to N. These couples are connected N to P at the opposite end. The probe tip junctions 10, 10', 10", etc. represent one set of junctions. The other set of junctions are the reference junctions 12, 12', 12", 12"', etc.

The electrical connection of the legs may be achieved by connecting the dissimilar legs directly together. A third material, preferably a highly conductive material, may be used to join the two electrodes, or to connect the electrodes to external control and sensing circuitry A preferred embodiment for the unicouple design shown in FIG. 2A utilizes a molybdenum silicide plate to join the electrodes at the probe tip junctions 10, 10'. The molybdenum silicide plate which connects the electrodes at the probe tip junctions 10, 10' is referred to as a hot junction "shoe" 11.

A preferred emodiment for the multicouple design shown in FIG. 2B utilizes molybdenum silicide plates to join the legs at the probe tip junctions 10, 10', 10", 10"', 10"", 10""'. The molybdenum silicide plates which connect the electrodes at the probe tip junctions are referred to as hot junction "shoes" 11, 11', 11". Metal plates or bars, referred to as cold junction "shoes" 13, 13', are used to connect the legs at the reference junctions 12, 12', 12", 12"'.

The thermoelectric element 7 (FIG. 1) may include a reference temperature sensor 27 to measure the temperature at a reference junction. An example of a reference temperature sensor 27 is a platinum wire having a resistance which varies with temperature in a known way. The connector wires 14, 14' and sensor wires 28, 28' leading out from the reference temperature sensor 27 are typically copper wires.

Referring to the unicouple design, as representative of the present invention, thermoelectric heating of the probe tip junctions 10, 10' (see FIG. 1) occurs when an electrical current is passed through the couple in the P to N direction. The reference junctions 12, 12' experience cooling when this electrical current is passed through the couple.

Figure 1:
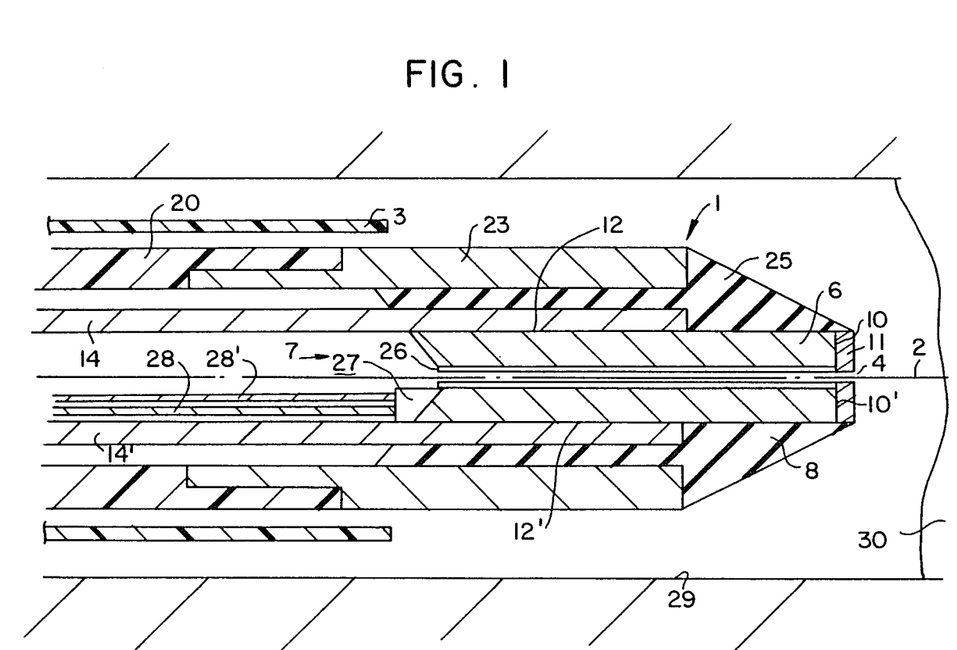
FIG. 1 is a side view, in section, of a tip-heated probe, in accordance with the present invention, shown within a patient's artery.

Additional Joulean heating occurs in the electrodes 6, 8 because of the internal resistance of the legs. This Joulean heating enhances the heating of the hot junction shoe 11, but diminishes the cooling at the reference junction 12, 12'.

The electrical current fed to the couple through connector wires 14, 14' is periodically interrupted. An "open circuit" voltage is generated which is dependent on the difference in temperature between the probe tip junctions 10, 10' and the reference junctions 12, 12'. Thus, the temperature of the probe tip junctions 10, 10' may be determined from a known temperature of the reference junctions 12, 12' and the measured "open circuit" voltage.

Precise temperature control of the probe 1 is possible through the selection of materials for the legs with high thermoelectric potentials and low electrical resistivity. In other words, a high signal-to-noise ratio is produced in a measured Seebeck voltage since materials with high thermoelectric potentials and low electrical resistivity produce high signal voltages and low resistive (Johnson) noise. Noise is produced by P and N carriers (so called generation-recombination noise), which is proportional to the current. Increasing the electrical resistivity of the material increases the Joulean heating thereby reducing the electrical current required to achieve a given power dissipation.

Incorporating many thin legs in the thermoelectric element 7, as in the multicouple configuration shown in FIG. 2B, increases the number of junctions and the thermoelectric output. The resistance of the element 7 also increases due to the reduction of the electrodes' cross-sectional areas, so that the signal-to-noise ratio may increase or decrease depending on the exact area achieved. The drive current can be reduced to almost any level by increasing the number of legs within the same element volume. It is important that the available volume for the hot junction shoe 11 be filled with active materials (P or N), and that the amount of insulating material or mounting substrates used in the probe 1 be reduced as much as possible to achieve efficient heating.

The hot junction shoe 11 acts as an interconnection between P and N legs 6, 8 in a single couple (unicouple) design. In this way, the heat generated is conveyed to the point of application, and the temperature of the hot junction shoe 11 is most accurately determined. This hot junction shoe 11 is maintained at electrical ground (zero volts). The P and N legs 6, 8 of the thermoelectric element 7 are separated by a thin layer of insulating material 26, such as high temperature glass, which closely matches the thermal expansion coefficient of the leg materials. This insulating material 26 may be penetrated by a hole 4 through which a guide wire 2 can be passed.

Precise temperature control of the hot junction shoe 11 requires that the temperature at the reference junction 12, 12' be known and stable. This can be accomplished with a reference temperature sensor 27 described previously. The reference junctions 12, 12' can also be thermally connected to a metal sleeve 23 that is electrically isolated from the legs 6, 8 and from the hot junction shoe 11 with glass or ceramic insulating material 25 to achieve this same goal. This insulating material 25 and metal sleeve 23 provide the thermal conductivity and contact area needed to hold the reference junctions 12, 12' at a constant body temperature, while providing a benign interface (e.g. stainless steel) to the living tissue. The reference junctions 12, 12' are then maintained at the surrounding temperature and the need for a reference temperature sensor 27 is thus eliminated. The large surface area of the reference junctions 12, 12' insures a stable temperature at the reference junctions 12, 12'. The temperature at the probe tip junctions 10, 10' differs slightly from the temperature on the outer surface of the hot junction shoe 11. This small temperature gradient is fully predictable.

In a preferred embodiment, the probe 1 has an outer diameter of about 0.065 inches, the hot junction shoe 11 is approximately a 0.030 inch by 0.030 inch square, the hole 4 has a diameter of about 0.015 inches, and a sheath 3 has an outer diameter of approximately 0.08 inches. Another embodiment provides for a hole 4 to be located adjacent to one side of the thermoelectric element 7 rather than between the legs 6, 8. This configuration permits a hole 4 having a larger diameter to be utilized to accommodate a guide wire 2 having a large diameter. This configuration also allows greater amounts of active P and N materials in the legs for a specified overall probe diameter.

The probe 1 is designed to attach to the end of a conventional catheter 20. The catheter 20, modified in accordance with the present invention, and an extendable guide wire 2 are advanced through a catheter sheath 3 into a patient's artery 29 or through a hypodermic needle (not shown). The guide wire 2 is directed down the artery 29 with the use of X-rays to monitor its progress. When an arterial obstruction 30 is reached by the guide wire 2, the catheter 20 is extended over the length of the guide wire 2. The probe 1 is used to melt or to vaporize the obstruction 30. After the obstruction 30 is eliminated, the catheter 20 with the attached probe 1, the sheath 3, and the guide wire 2 are removed.

Figure 3:
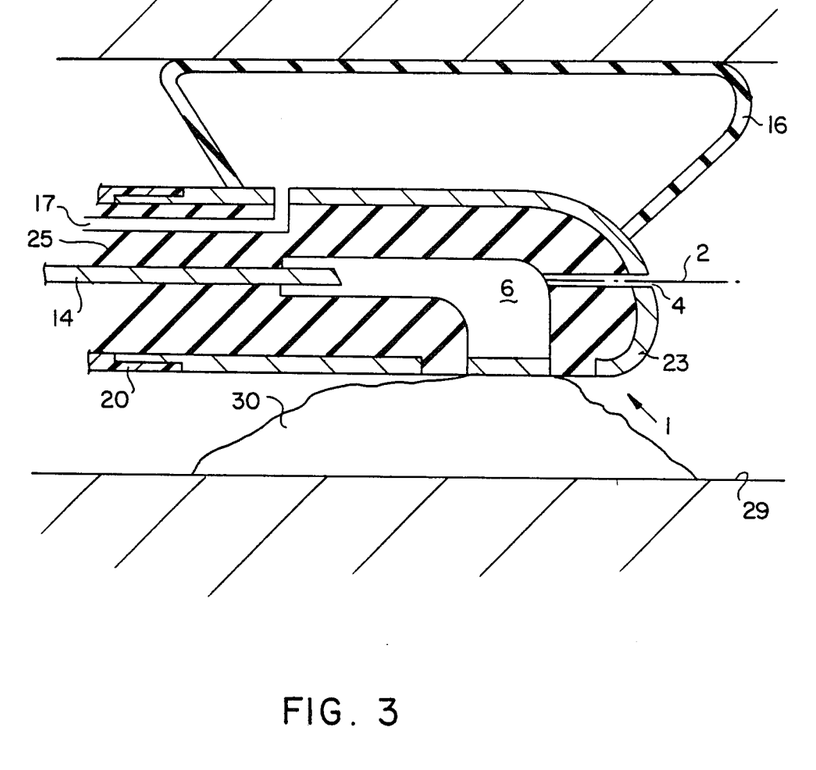
FIG. 3 is a side view, in section, of a side-heated probe, in accordance with the present invention, shown pressed by a balloon against a deposit within a patient's artery.
Figure 4:
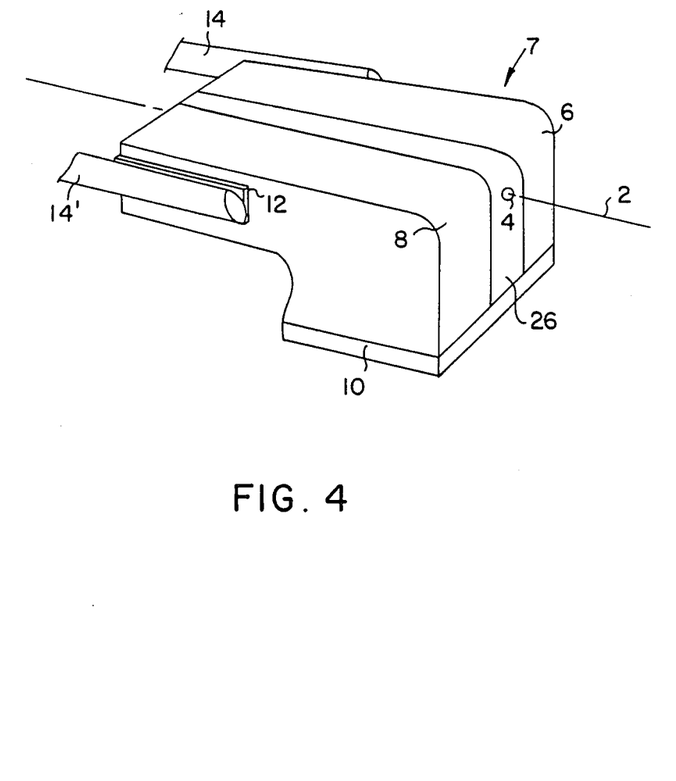
FIG. 4 is a view in perspective of a thermoelectric element used in a side-heated probe in accordance with the present invention.

The thermoelectric element 7 can be configured to provide heating or cooling at the distal end of an elongated probe, as discussed previously in reference to FIG. 1. Another embodiment of the present invention, shown in FIGS. 3 & 4, provides heating or cooling from the side of an elongated probe. In the side heating embodiment, the thermoelectric element 7 can be configured so that the hot junction shoe 11 is located at the side wall of the probe. One or more balloons 16 can be positioned against the arterial wall 29, across from the hot junction shoe 11, so as to press the hot junction shoe 11 against the obstruction 30 when inflated In another embodiment, the balloon(s) 16 are bound to the probe 1 and inflated through a balloon inflation tube 17 (see FIG. 3). The balloon inflation tube 17 is defined by the insulating material 25.

Figure 5:
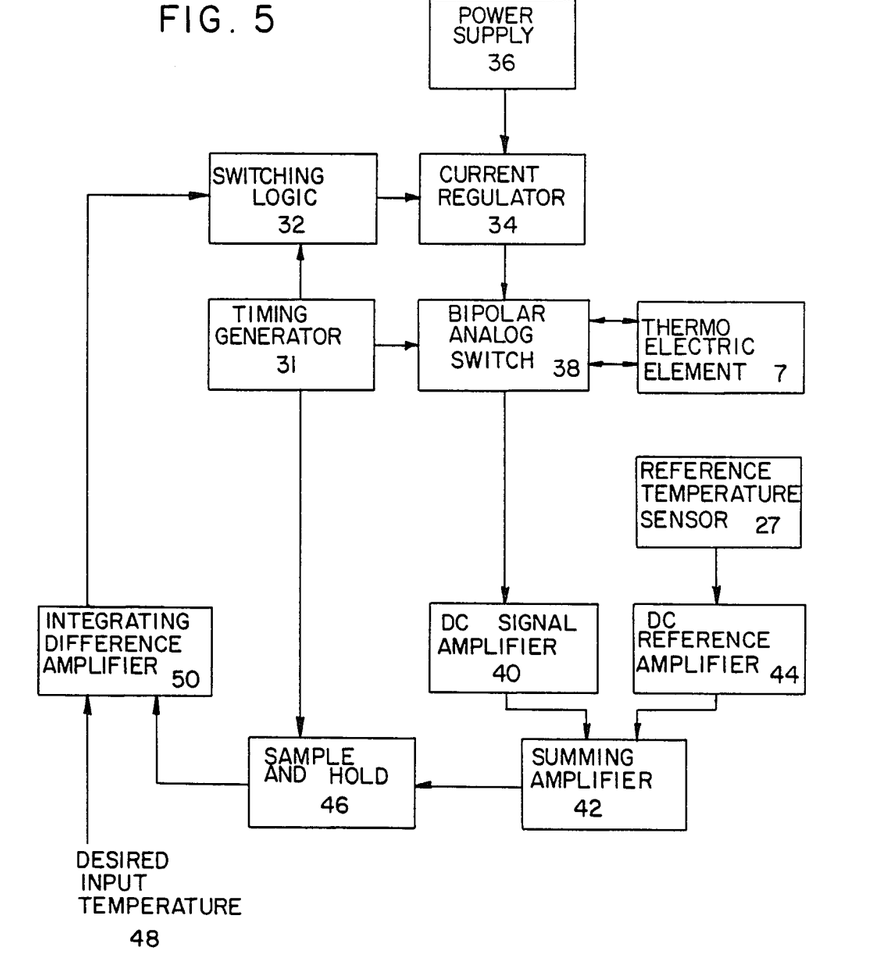
FIG. 5 is a schematic view of the temperature sensing and control circuitry of the present invention.

A preferred heating and control circuit for the thermoelectric element 7 of the invention is shown in block diagram form in FIG. 5. A timing generator 31 operates at a frequency which defines the time allocated to monitor the Seebeck voltage. (The time required to measure the Seebeck voltage can be as short as a few microseconds.) The timing generator 31 also operates switching logic 32. The switching logic 32 controls a current regulator 34. The current regulator 34 regulates the heating or cooling power based on the fractional time the current is on, called the duty cycle. Preselected, controlled heating or cooling currents are provided from a power supply 36 through the current regulator 34 and through a bipolar analog switch 38 to the thermoelectric element 7. The present invention is capable of providing rapid cooling after heating is completed by reversing the drive voltage polarity. The bipolar analog switch 38 routes the current through the thermoelectric element 7 in either the heating or cooling direction, and shuts off the power supply 36 when the power supply 36 is at zero volts output so that a D.C. signal amplifier 40 can then be connected to the thermoelectric element 7 to obtain a differential temperature measurement between the reference junctions 12, 12' and the probe tip junctions 10, 10'.

A summing amplifier 42 combines the output of a D.C. reference amplifier 44, which monitors a reference temperature sensor 27, with the output of the D.C. signal amplifier 40, which measures the temperature difference between the probe tip junctions 10, 10' and the reference junctions 12, 12', allowing the absolute temperature at the probe tip 10 to be determined. (If the reference junctions 12, 12' are adequately maintained at body temperature through thermal conduction, the D.C. reference amplifier 44 and the summing amplifier 42 can be omitted.) The timing generator 31 also controls a sample and hold circuit 46. The sample and hold circuit 46 receives the output of the summing amplifier 42 during the sample time and maintains that signal level until updated during the next sample time. This sampled signal level is compared with a desired input temperature 48 in an integrating difference amplifier 50. This amplifier 50 provides a control signal to the switching logic circuit 32 which converts the control amplitude into a time (duty cycle) and varies the switching signal to operate the current regulator 34.

Ultimate control of the temperature at the hot junction shoe 11 is provided as the desired input temperature 48 through manual selection, or through a minicomputer program which permits one or more very rapid, preselected sequence of temperatures to be provided on each command.

Figure 6:
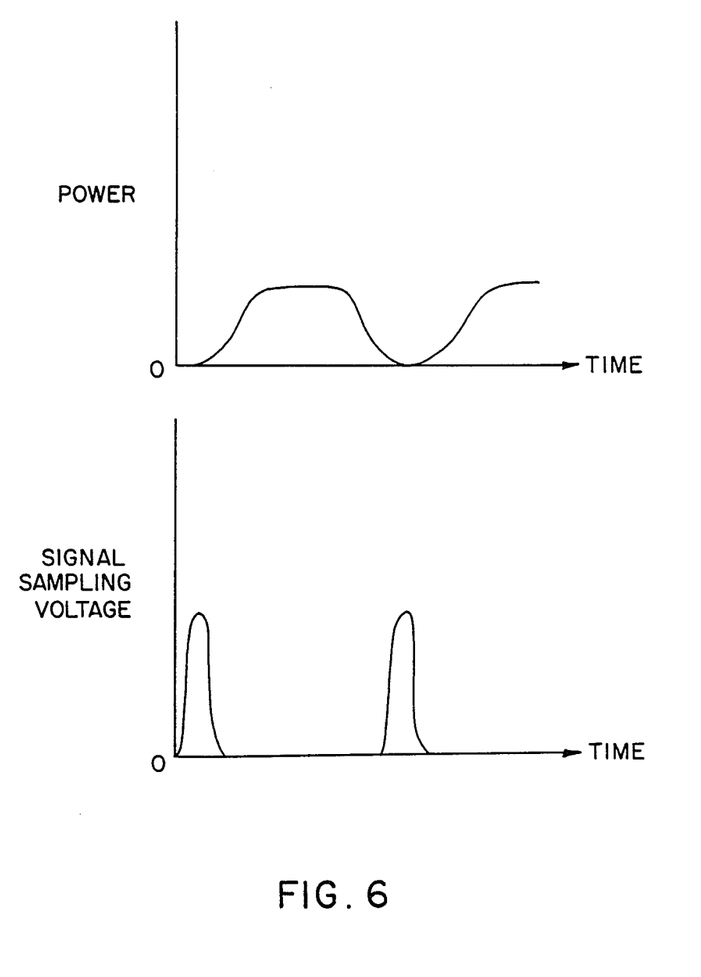
FIG. 6 is a diagram of a power and sensing relationship of the invention with respect to time.

In controlling the heating power transmitted to the thermoelectric element 7, it is essential to avoid high frequency electromagnetic radiation that could result from the abrupt switching of this power (and interfere with the function of a patient's pacemaker, for example). The most suitable approach is the generation of a smoothly varying power amplitude controlled to avoid reversing polarity (which would result in unintended tip cooling). A suitable signal waveform is shown in FIG. 6. It can be seen that the sampling is done at the point in the waveform where the power signal is zero. This is done because the Peltier effect signal is dominated by the voltages present when high currents pass through the device.

EXAMPLE

An example of a minicomputer programmed command sequence in accordance with the present invention would be to raise the temperature of the probe tip 10 very rapidly (e.g. in about 0.05 seconds) to 380° C., called accelerated heating, then hold this temperature for 0.2 seconds, which vaporizes the plaque, then drop the temperature linearly to 225° C. over the next 0.3 seconds, permitting the plaque to liquify, and finally to reverse the polarity and cool the probe tip 10 to blood ambient at 37° C. in 0.05 seconds, called accelerated cooling. It is also possible to inflate and deflate the balloon(s) 16 under computer control. For example, the balloon(s) 16 would be inflated during the accelerated heating phase, the inflation would be maintained during the vaporization and liquification phases, and the balloon(s) would be deflated during the accelerated cooling phase. Verification of the measured probe tip temperature variation can be displayed on a computer monitor screen in real time.

EXAMPLE

In an experiment, the entire length of an arterial segment, having a heavily calcified thrombus and plaque causing total occlusion of the lumen, was suspended in a beaker filled with water. A successful recanalization of the lumen was achieved using an Anand Catheter similar to that shown and described herein with reference to FIG. 1. Histologic studies revealed recanalization of the calcified thrombus and the plaque without significant injury to the media or adventitial layers of the artery. This study shows that the temperature required to achieve recanalization of an artery occluded with calcified plaque can be achieved with this device. It also shows that an optimal temperature can be maintained in liquid medium which could otherwise act as a heat sink. The study also demonstrates that the recanalization of the artery was achieved without significant thermal injury to the arterial wall.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and there is no intention to exclude any equivalence thereof. Hence, it is recognized that various modifications are possible when within the scope of the present invention as claimed.

What is claimed is:

1. An apparatus for applying highly controlled, localized heating or cooling to precise points in a patient to treat the patient comprising:
   a P-doped thermocouple leg including first and second end portions and an N-doped thermocouple leg including first and second end portions, said legs being connected at said first end portions to form a probe tip junction and not being connected at said second end portions, said legs being oriented to be opposite each other;
   a metal sleeve surrounding said unconnected second end portions of said thermocouple legs;
   a layer of thermally conductive, electrically insulative material separating said thermocouple legs from said metal sleeve;
   means for delivering said pair of thermocouple legs into a patient's body; and
   means for passing a current through said pair of legs to heat or cool said probe tip junction.

2. The apparatus of claim 1 wherein said metal sleeve is bonded to an end of a catheter and said first end portions forming said probe tip junction extend from said catheter.

3. The apparatus of claim 1 wherein said pair of thermocouple legs are constructed from materials having a high thermoelectric potential and a low electric resistivity.

4. The apparatus of claim 1 wherein said pair of thermocouple legs are constructed from semiconductor material.

5. The apparatus of claim 1 wherein said pair of thermocouple legs are constructed from a semiconductor material selected from the group consisting of silicon and alloys of silicon and germanium.

6. The apparatus of claim 1 including a molybdenum silicide plate joined to said first end portions of the pair of thermocouple legs to form said probe tip junction.

7. The apparatus of claim 1 including a pair of connector wires individually attached to the pair of thermocouple legs near said second end portion remote from said first end portion to form a pair of reference junctions.

8. The apparatus of claim 7 including means for determining and controlling the temperature of said probe tip junction.

9. The apparatus of claim 8 wherein said means for determining and controlling the temperature of said probe tip junction includes a temperature sensor thermally connected to at least one of the thermocouple legs at a location away from said probe tip junction and means for periodically interrupting the flow of current through said thermocouple legs.

10. The apparatus of claim 1 having more than one pair of thermocouple legs.

11. The apparatus of claim 10 wherein said more than one pair of thermocouple legs are constructed from semiconductor material.

12. The apparatus of claim 10 wherein said more than one pair of thermocouple legs are constructed from a semiconductor material selected from the group consisting of silicon and alloys of silicon and germanium.

13. The apparatus of claim 10 wherein each of said thermocouple legs is electrically separated along its length.

14. The apparatus of claim 10 wherein said more than one pair of thermocouple legs are joined at a first end in pairs P to N.

15. The apparatus of claim 14 wherein said more than one pair of thermocouple legs are joined at a second end in pairs N to P.

16. The apparatus of claim 1 wherein said layer of thermally conductive, electrically insulative material which insulates said thermocouple legs from said metal sleeve defines a channel through said apparatus substantially parallel to said legs to accommodate a guide wire.

17. The apparatus of claim 1 wherein said thermocouple legs are bent such that said probe tip junction faces perpendicularly to a longitudinal axis of said apparatus.

18. The apparatus of claim 17 including a balloon positioned adjacent to a probe tip adjacent to said probe tip junction, said balloon being inflatable within an artery to press said probe tip junction against said facing arterial wall.

19. The apparatus of claim 17 wherein the pair of thermocouple legs are constructed from materials having a high thermo-electric potential and low electrical resistivity.

20. The apparatus of claim 17 wherein the pair of thermocouple legs are constructed from a semiconductor material.

21. The apparatus of claim 17 wherein the pair of thermocouple legs are constructed from a semiconductor material selected from the group consisting of silicon and alloys of silicon and germanium.

22. The apparatus of claim 17 including a molybdenum plate joined to said first end portions of the pair of thermocouple legs to form said probe tip junction.

23. The apparatus of claim 17 including a pair of connector wires individually connected to the pair of thermocouple legs near said second end portions remote from said first end portions to form a pair of reference junctions.

24. The apparatus of claim 17 having more than one pair of thermocouple legs.

25. The apparatus of claim 24 wherein said more than one pair of thermocouple legs are constructed from semiconductor material.

26. The apparatus of claim 24 wherein said more than one pair of thermocouple legs are constructed from a semiconductor material selected from the group consisting of silicon and alloys of silicon and germanium.

27. The apparatus of claim 24 wherein each of said thermocouple legs is electrically separated along its length.

28. The apparatus of claim 24 wherein said more than one pair of thermocouple legs are joined at a first end in pairs of P to N.

29. The apparatus of claim 24 wherein said more than one pair of thermocouple legs are joined at a second end in pairs N to P with metal plates.

30. The apparatus of claim 24 wherein a P-doped leg and an N-doped leg of said more than one pair of thermocouple legs are attached to two connector wires.

31. The apparatus of claim 1 including means for determining and precisely controlling the temperature of said probe tip junction.

32. An apparatus for applying highly controlled localized heating to precise joints within a patient to melt or vaporize undesirable organic material comprising:

a probe tip including a P-doped leg of semiconductor thermoelectric material having first and second end portions and an N-doped leg of semiconductor thermoelectric material having first and second end portions arranged substantially parallel to said P-doped leg and electrically insulated from said P-doped leg along the lengths of said legs, an electrically conductive shoe connected to said first end portions of said legs to form a probe tip junction, said legs being unconnected at their second end portions, a first electrical lead attached to said P-doped leg to form a first reference junction, and a second electrical lead attached to said N-doped leg to form a second reference junction;

a metal sleeve surrounding said second end portions of said legs;

a layer of thermally conductive, electrically insulative material separating said thermocouple legs from said metal sleeve;

means for delivering said probe tip to a selected location within the body of a patient; and means for passing an electrical current through said electrical leads and said legs to heat said shoe to a selected temperature sufficient to melt or vaporize undesirable organic material at said selected location and for precisely controlling the temperature of said shoe.

* * * * *